US007335625B2

(12) United States Patent
Tynik

(10) Patent No.: US 7,335,625 B2
(45) Date of Patent: Feb. 26, 2008

(54) ORGANOAMMONIUM TUNGSTATE AND MOLYBATE COMPOUNDS, AND PROCESS FOR PREPARING SUCH COMPOUNDS

(75) Inventor: Robert J. Tynik, Norwalk, CT (US)

(73) Assignee: R.T. Vanderbilt Company, Inc., Norwalk, CT (US)

(*) Notice: Subject to any disclaimer, the term of this patent is extended or adjusted under 35 U.S.C. 154(b) by 550 days.

(21) Appl. No.: 10/822,057

(22) Filed: Apr. 8, 2004

(65) Prior Publication Data

US 2004/0214731 A1 Oct. 28, 2004

Related U.S. Application Data

(60) Provisional application No. 60/464,541, filed on Apr. 22, 2003, provisional application No. 60/517,604, filed on Nov. 5, 2003.

(51) Int. Cl.
*C10M 159/18* (2006.01)
*C01G 41/02* (2006.01)

(52) U.S. Cl. .................. 508/362; 508/167; 423/594.13

(58) Field of Classification Search ................ 508/362, 508/167; 423/594.13
See application file for complete search history.

(56) References Cited

U.S. PATENT DOCUMENTS 3,114,712 A * 12/1963 Spengler et al. ............ 508/362
3,282,838 A 11/1966 Knowles et al.
3,489,775 A * 1/1970 de Roch et al. ............ 549/529
4,217,292 A 8/1980 Kroenke ..................... 260/429
4,234,473 A 11/1980 Kroenke .................. 260/45.74
4,261,843 A 4/1981 King et al.
4,406,837 A 9/1983 Kroenke ..................... 260/429
4,410,463 A 10/1983 Kroenke .................. 260/45.75
4,424,164 A 1/1984 Kroenke ..................... 260/429
4,626,367 A * 12/1986 Kuwamoto et al. .......... 508/156
4,692,256 A 9/1987 Umemura et al.
4,780,553 A 10/1988 Suzuki et al. ................. 556/26
5,308,519 A 5/1994 Spiess et al. .............. 252/46.4
5,319,119 A 6/1994 Kaneshima et al.
5,364,951 A 11/1994 Soncini et al. ................. 556/9
5,652,201 A * 7/1997 Papay et al. ................ 508/228
5,716,913 A 2/1998 Yamamoto et al.
5,858,931 A 1/1999 Tanaka et al.
6,329,327 B1 12/2001 Tanaka et al.
2003/0119682 A1* 6/2003 Saini et al. ................. 508/167

OTHER PUBLICATIONS

Errington, R. J., Chem. Soc., Chem. Commun., 1993, 649-651.*

Freedman, M. L., J. Am. Chem. Soc., 1959, 81, 3834-3839.*

Krause, A. C., and Krauskopf, F. C., J. Am. Chem. Soc., 1925, 1689-1694.*

Curran, Timothy P. et al., Pi-Ligands for Generating Transition Metal-Peptide Complexes: Coordination of Amino Acid Derivatives to Tungsten Utilizing Alkyne Ligands, 2002, Organic Letters, 4 (17): 2917-2920; Abstract: Accession No. 137:263138.

Galakhov, Mikhail V. et al., Cyclopentadienyl dithiocarbamate and dithiophosphate molybdenum and tungsten complexes, J. of Organometallic Chemistry, 1999, 579 (1-2): 190-197; Abstract: Accession No. 131:185049.

Long, De-Liang et al., Synthesis and Crystal Structure of [P(CH2Ph)Ph3] [PdWS4 (S2CNC4H8)], Jiegou Huaxue, 1998, 17(2): 155-158; Abstract: Accession No. 128:330307.

Sharma, R.C. et al., Synthetic and antibacterial studies of some binuclear compounds of tungsten, J. of Institution of Chemists (India), 1997, 69(1): 16-17; Abstract: Accession No. 127:116652.

Cao, Rong et al., Syntheses, structures and spectroscopic properties of Mo(W)-Cu-S-cluster compounds with dialkyldithiocarbamate ligands, 1995, Jiegou Huaxue, 14(1): 33-43; Abstract: Accession No. 122:229121.

Feng, S.G. et al., Unsaturated carbene ligards: (*n*4-butadienyl)tungsten dithiocarbamate complexes, 1989, Organometallics, 8(8): 2024-2031; Abstract: Accession No. 111:77931.

Burgmayer, Sharon Josephine Nieter, Syntheses, structures and chemistry of molybdenum and tungsten carbonyl dithiocarbamates, 1984, Diss. Abstr. Int. B 1985, 45(8), 2546; Abstract: Accession No. 102:178069.

Glass, W.K. et al., Mononuclear pi-cyclopentadienyltungsten dicarbonyl dithiocarbamates, J. of Organometallic Chemistry, 1974, 67(3): 401-405; Abstract: Accession No. 80:133577.

International Search Report for corresponding PCT application No. PCT/US04/10994 dated Aug. 18, 2004.

* cited by examiner

*Primary Examiner*—Vasu Jagannathan
*Assistant Examiner*—Jim Goloboy
(74) *Attorney, Agent, or Firm*—Norris, McLaughlin & Marcus

(57) ABSTRACT

Novel organoammonium compounds are provided, which are useful as additives for improving the antiwear and friction-reducing properties of lubricating compositions. The compound is formed by reacting a metal acid hydrate with one or more alkyl amines. Particular examples are the preparation of ditridecylammonium tungstate, di-n-octylammonium tungstate and ditridecylammonium molybdate.

10 Claims, No Drawings

ORGANOAMMONIUM TUNGSTATE AND MOLYBATE COMPOUNDS, AND PROCESS FOR PREPARING SUCH COMPOUNDS

This application is a non-provisional of provisional application Nos. 60/464,541 filed Apr. 22, 2003, and 60/517,604, filed Nov. 5, 2003.

BACKGROUND OF INVENTION

1. Field of the Invention

The present invention relates to lubricant additives for imparting antifriction and antiwear properties. In particular, the invention relates to novel organoammonium tungstate and molybdate compounds and the process for preparing such compounds, as well as lubricating compositions containing such compounds.

2. Prior Art

The development of lubricants represents an important area of technology geared toward finding ways to reduce friction between contacted moving components in various mechanical devices. The mechanical wear of these components is greatly accelerated by friction, thus, increasing the expense of operating mechanical devices. In the context of engines, such as automotive engines, using lubricants to reduce the internal friction in the engine has the added benefit of reducing the engine's energy requirements. This friction increases the power required to effect movement, thus increasing fuel consumption and decreasing mileage. It is now clearly appreciated that it is advantageous to use lubricants to minimize friction in many types of mechanical devices.

Antifriction additives perform their functions by different physical or chemical mechanisms. Therefore, in the context of lubricating internal engines it is especially desirable that the additive possesses other functional properties, such as those associated with reducing the physical wear of mechanical components.

Molybdenum dithiocarbamate is currently used as an additive to lubricating oils for imparting antiwear and antifriction properties. While this composition is effective, a relatively high amount of the composition is required to achieve the desired properties. Therefore, there is a desire for compounds that achieve equal or better effect, yet require a lower amount of additive.

SUMMARY OF THE INVENTION

It has been now discovered that a novel class of organoammonium metal compounds imparts added antifriction and antiwear properties to lubricants. The invention further relates to a process for preparing these organoammonium metal compounds. The organoammonium metal compounds described, based on Group VI metals such as molybdenum or tungsten, have been shown to improve the lubricating properties of such lubricating oils when added to the oil at a final concentration of 0.025 to 5.0 wt.-%, based on the total weight of the lubricating composition. However, in comparison to the prior art compounds, the novel compounds of the invention can achieve excellent properties with a much lower amount of metal required. The compounds are the reaction product of the method described below, and are believed to be dialkylammonium molybdates or tungstates.

The method of preparing the organoammonium metal compound is also described. In brief, the compound is formed by reacting a metal acid hydrate with one or more alkyl amines. Particular examples are the preparation of ditridecylammonium tungstate, di-n-octylammonium tungstate and ditridecylammonium molybdate. The invention also relates to novel compounds formed as the reaction product of tungstic or molybdic acid hydrate with a secondary amine, as well as to lubricating composition containing such compounds.

DETAILED DESCRIPTION

The process is described below in conjunction with the reaction diagram shown. While the preparation of ditridecylammonium tungstate, di-n-octylammonium tungstate and ditridecylammonium molybdate are shown as illustrative embodiments, preparation of other dialkylammonium tungstates and molybdates is envisioned, and the skilled artisan will understand that this can be achieved by starting with a corresponding amine. It is also envisioned that this process will be useful for dialkylammonium salts based on other Group VI metals, such as tellurium and selenium. The skilled artisan will also understand that variations in the processing parameters may be made without departing from the scope or spirit of the invention.

Preparation of Organoammonium Salts of Tungsten and Molybdenum

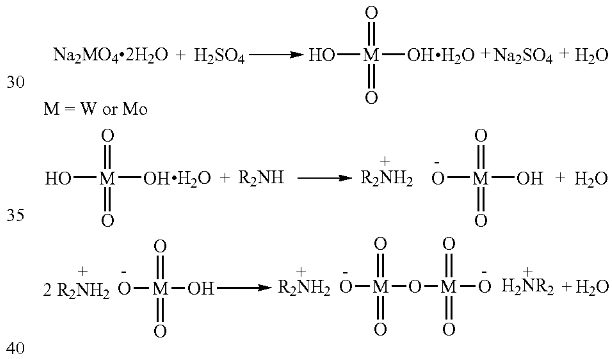

In general, the process for preparing the organoammonium metal compounds of the invention involves converting an alkali metal dihydrate of a Group VI metal; e.g., sodium tungstate dihydrate, to the corresponding metal acid hydrate of the Group VI metal. The metal acid hydrate is then reacted with an alkyl amine to form the organoammonium compound of the invention.

A particular example of the process of the invention is as follows: Sodium tungstate dihydrate (66.0 g., 0.200 mole) is dissolved in water (150 g.). The sodium tungstate dihydrate may be used per se as the starting material, or this may be prepared by reacting tungsten trioxide with sodium hydroxide, or other known methods. A solution of 96% sulfuric acid (20.6 g., 0.202 mole) dissolved in water (50 g.) is then slowly added with good agitation to the sodium tungstate dihydrate solution to generate tungstic acid hydrate. Temperature is not critical for this reaction and can vary from about 10-70 degrees C., with a preferred range of about 20-50 degrees C.

It is important that the tungstic acid hydrate is prepared because the hydrate is appreciably soluble in water, and although some may precipitate from solution, it precipitates in a very finely divided form. Both the dissolved and the precipitated material are in a form that will react rapidly and completely in the next step when the amine is added. Tungstic acid solid can also be used but the reaction with amines is much slower and requires prolonged heating times because of the much larger particle size.

After the tungstic acid hydrate is generated, an organic solvent, e.g., heptane (100 g.) is added, followed by ditridecylamine (77.7 g., 0.20 mole) using good agitation during the additions. Temperature is not critical for this reaction, which is slightly exothermic, and can vary from about 10-70 degrees C., with a preferred range of about 20-50 degrees C. The reaction mixture is then heated to reflux for about 30 minutes to ensure complete conversion to what is believed to be di-nuclear ditridecylammonium tungstate.

The reflux time may vary according to the specific amine being used. In the present specific example producing ditridecylammonium tungstate product, a reflux time of 30 minutes was effective, but substantially longer reflux times may be required, especially if the specific amine is sterically hindered.

After the reflux period is complete, the mixture is transferred to a separatory funnel and the two phases are allowed to separate into an upper, product layer and a lower, aqueous sodium sulfate layer. The lower layer is drained out and then the product layer is drained into a round-bottom flask. The product layer is rotary evaporated to remove the heptane and any traces of water leaving 126.0 g. of a viscous liquid. This liquid is then filtered hot (80-90° C.) to remove any small amounts of solid material, such as sodium sulfate crystals, leaving a clear, viscous, light-yellow liquid product.

Another particular example of the process is as follows: Sodium tungstate dihydrate (66.0 g., 0.200 mole) is dissolved in water (150 g.). A solution of 96% sulfuric acid (20.6 g., 0.202 mole) dissolved in water (50 g.) is then slowly added with good agitation to the sodium molybdate dihydrate solution to generate a solution of tungstic acid hydrate. Temperature is not critical for this reaction and can vary from about 10-70 degrees C., with a preferred range of about 20-50 degrees C. After the tungstic acid hydrate is generated, an organic solvent, e.g., toluene (100 g.) is added followed by di-n-octylamine (49.3 g., 0.20 mole) using good agitation during the additions. Temperature is not critical for this reaction, which is slightly exothermic, and can vary from about 10-70 degrees C., with a preferred range of about 20-50 degrees C. The reaction mixture is then heated to reflux for about 20 minutes to ensure complete conversion to what is believed to be di-nuclear di-n-octylammonium tungstate. After the reflux period is complete, the mixture is transferred to a separatory funnel and the two phases are allowed to separate into an upper, product layer and a lower, aqueous sodium sulfate layer. The lower layer is drained out and then the product layer is drained into a round-bottom flask. The product layer is rotary evaporated to remove the toluene and any traces of water leaving 97.8 g. of an off-white, waxy solid.

Another particular example of the process is as follows: Sodium molybdate dihydrate (48.4 g., 0.200 mole) is dissolved in water (150 g.). A solution of 96% sulfuric acid (20.6 g., 0.202 mole) dissolved in water (50 g.) is then slowly added with good agitation to the sodium molybdate dihydrate solution to generate a solution of molybdic acid hydrate. Temperature is not critical for this reaction and can vary from about 10-70 degrees C., with a preferred range of about 20-50 degrees C. After the molybdic acid hydrate is generated, heptane (100 g.) is added followed by ditridecylamine (81.6 g., 0.20 mole) using good agitation during the additions. Temperature is not critical for this reaction, which is slightly exothermic, and can vary from about 10-70 degrees C., with a preferred range of about 20-50 degrees C. The reaction mixture is then heated to reflux for about 30 minutes to ensure complete conversion to what is believed to be di-nuclear ditridecylammonium molybdate. After the reflux period is complete, the mixture is transferred to a separatory funnel and the two phases are allowed to separate into an upper, product layer and a lower, aqueous sodium sulfate layer. The lower layer is drained out and then the product layer is drained into a round-bottom flask. The product layer is rotary evaporated to remove the heptane and any traces of water leaving 111.9 g. of a very viscous, blue-green liquid that solidifies to a gray-green, waxy solid upon cooling to room temperature.

Liquid forms of the solid products can be prepared by mixing them with any suitable diluent liquid and agitating at elevated temperatures until the product has completely dissolved. The liquid forms can then be suction filtered to remove any solid impurities.

The amounts of the starting materials should not be varied so much as to negatively affect either product quality or yield. However, because the tungsten and molybdenum starting materials are the most expensive, the other starting materials are normally used in a small excess to ensure that all of the tungsten or molybdenum is consumed.

It is expected that, for the $R_2NH$ used in the reaction, any secondary amines of the formula $R^1R^2NH$ where $R^1$ and $R^2$ can be the same or different and are selected from linear or branched, saturated or unsaturated $C_2$-$C_{40}$ alkyl groups, $C_3$-$C_{40}$ cycloalkyl groups, $C_6$-$C_{40}$ aryl groups, $C_7$-$C_{40}$ alkaryl and aralkyl groups will work unless there is significant steric hindrance near the amine nitrogen. It has been found that the reaction of tungstic acid hydrate, and to a lesser extent molybdic acid hydrate, with the specific amine is sensitive to steric hindrance near the amine nitrogen. When amines with straight alkyl chains, such as di-n-octylamine and ditridecylamine, are used, near quantitative yields can be expected. Therefore, while it is possible to use the process described based on dialkylamines in general, it is preferred to utilize amines based on sterically unhindered alkyl chains ranging from $C_2$ to $C_{40}$, even more preferably from $C_5$ to $C_{18}$.

Mixtures of two or more different amines can also be used as well as monoalkylamines, with the expected result being an unsymmetrical monoalkyl or dialkyl ammonium tungstate or molybdate. Multi-functional amines, such as diamines and triamines, can also be used.

The invention also relates to the reaction products obtained from the above process, as well as lubricating compositions containing said reaction products. From the data below, it is seen that the compounds will be particularly useful for enhancing friction reduction and antiwear properties of lubricants when added to lubricating compositions in the amount of 0.025 to 5.0 mass percent, preferably about 0.05 to 2.0% and more preferably from about 0.09 to 0.5% based on the weight of the lubricating composition. It is expected that the inventive products will have positive anti-oxidation effect, and that they may also act as extreme pressure agents. For ease of incorporation into the lubricating formulation, the reaction product can be dissolved in or diluted with a diluent compatible with the lubricating formulation. The base oil of the lubricants may be selected from naphthenic, aromatic, paraffinic, mineral and synthetic oils. The synthetic oils may be selected from, among others, alkylene polymers, polysiloxanes, carboxylic acid esters and polyglycol ethers.

The lubricating compositions may contain the necessary ingredients to formulate the composition, as for example emulsifiers, dispersants and viscosity improvers. Greases may be prepared by adding thickeners, as for example, salts and complexes of fatty acids, polyurea compounds, clays and quaternary ammonium bentonite complexes. Depending on the intended use of the lubricant, other functional additives may be added to enhance a particular property of the lubricant. The lubricating compositions may further contain extreme pressure agents, metal passivators, rust inhibitors, dispersants and other known antioxidants and antiwear agents.

Experimental Data

BT-521-85A (50% di-nuclear ditridecylammonium tungstate in Uninap 100 SD oil) was evaluated. Results are compared to Molyvan®822 additive (molybdenum dithiocarbamate 50%, available from R.T. Vanderbilt Company, Inc.)

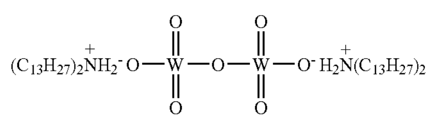

BT-521-85A

In Table 1, friction coefficient for the inventive compound di-nuclear ditridecylammonium tungstate was evaluated and compared to a presently used friction reducer, molybdenum dithiocarbamate. The data show an improvement in friction coefficient for the inventive tungsten compound compared to base oil without an additive. While the improvement is not as great as that for MoDTC, it is important to observe that the amount of tungsten compound needed to achieve an improvement in friction reduction effect is only ⅓ of the amount of MoDTC needed to deliver an equivalent amount of metal on a ppm basis. It is noted that both the W compound and the MoDTC were used at 50% dilution.

TABLE 1

| | Mass Percent | | |
|---|---|---|---|
| | A | B | C |
| BT-521-85A (14.8% W) | 0.46 | — | — |
| Molyvan ® 822 molybdenum dithiocarbamate (5.1% Mo) | — | 1.37 | — |
| GF-4 Prototype Motor Oil | 99.54 | 98.63 | 100 |
| ppm W or Mo (Approximate) | 700 | 700 | 700 |
| ASTM D5707 SRV Ball on Disc; 50 N, 50 N, 50 Hz; 1.00 mm Stroke 80° C.; 30 m; Final Friction Coefficient: | 0.111 | 0.054 | 0.134 |
| Appearance of Oil Blend | | | |
| After mixing @ RT | Clear | Clear | Clear |
| After 7 Day @ RT | Clear | Clear | Clear |

In Table 2, antiwear properties were compared for the inventive W compound and the prior art MoDTC compound. It can be seen that the W compound provides excellent antiwear protection, on par with that of MoDTC, while requiring only ⅓ of the amount of the W compound compared to MoDTC. It is also seen that the antiwear performance of the W compound does not necessarily improve as the amount in the lubricating compound is increased from 0.46 to 0.93 mass % of the diluted compound (0.23 to 0.465% on the basis of the W compound per se)

TABLE 2

| | Mass Percent | | | | | | |
|---|---|---|---|---|---|---|---|
| | A | B | C | D | E | F | G |
| BT 521-85A (14.8% W) | 0.46 | — | — | 0.46 | | 0.93 | — |
| Molyvan ® 822 molybdenum dithiocarbamate (5.1% Mo) | — | 1.37 | — | — | 1.37 | — | — |
| Uninap 100SD + Zinc dithiophosphate (0.1% P) | 99.54 | 98.63 | 100 | | | | |
| Exxon ® Blend ISO 220 | — | — | — | 99.54 | 98.63 | 99.07 | 100 |
| ppm W or Mo (Approximate) | 700 | 700 | 0 | 700 | 700 | 1,400 | 0 |
| ASTM D5707 SRV Ball on Disc; 50 N, 50 Hz; 1.00 mm Stroke 80° C.; 2 hours Final Friction Coefficient: | 0.110 | 0.060 | 0.121 | — | — | — | — |
| ASTM D-4172 4-Ball Wear 1200 rpm 75° C. 1 h @ 40 kgf, mm | — | — | — | 0.44* 0.48* | 0.52 | 0.45 | 1.42 |
| Appearance of Oil Blend | | | | | | | |
| After mixing at RT | Hazy | Clear | Clear | Hazy | Clear | Hazy | Clear |
| Next Day @ RT | Cloudy | Clear | Clear | Cloudy | Clear | Cloudy | Clear |

*two tests were run for formulation 4

BT 521-116A (50% di-nuclear ditridecylammonium molybdate in Corsol 100 oil) was evaluated. Results are compared to Molyvan® 855 (organo-molybdenum friction reducer, available from R.T. Vanderbilt Company, Inc.)

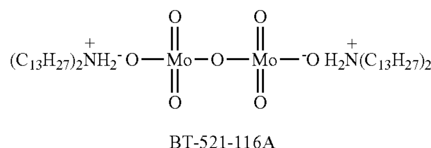

BT-521-116A

In Table 3 friction coefficient for the inventive compound di-nuclear ditridecylammonium molybdate was evaluated and compared to a presently used organo-molybdenum friction reducer. It can be seen that the inventive Mo compound provides excellent antifriction protection, nearly equivalent to that of Molyvan® 855, while requiring only ¼ to ½ of the amount of the inventive Mo compound compared to Molyvan® 855. It is also seen that the antifriction performance of the Mo compound does not necessarily improve as the amount in the lubricating compound is increased from 0.195 to 1.561 mass % of the diluted compound (0.098 to 0.781% on the basis of the inventive Mo compound per se).

TABLE 3

| | Mass Percent | | | | |
|---|---|---|---|---|---|
| | 1 | 2 | 3 | 4 | 5 |
| BT-521-116A | | | | | |
| 8.7% Mo: | 0.195 | 0.390 | 0.780 | 1.561 | — |
| MOLYVAN ® 855 | | | | | |
| 7.9% Mo: | — | — | — | — | 0.88 |
| ppm Mo: | 175 | 350 | 700 | 1400 | 700 |
| ASTM D5707 SRV | 0.095 | 0.093 | 0.105 | 0.124 | 0.082 |
| 200 N; 50 Hz; 80° C. | | | | | |
| 1 h; 1.00 mm Stroke: | | | | | |
| Ball on Disc | | | | | |
| Final Friction: | | | | | |
| Scar on | | | | | |
| Ball, mm: | 0.422 × 0.470 | 0.417 × 0.459 | 0.439 × 0.468 | 0.463 × 0.479 | 0.427 × 0.454 |
| Disc, mm: | 1.421 × 0.415 | 1.417 × 0.423 | 1.392 × 0.367 | 1.456 × 0.484 | 1.414 × 0.418 |

What is claimed is:

1. A lubricating composition comprising (a) a major amount of a lubricating oil, and (b) about 0.025 to 5.0 wt.-%, based on the total weight of the lubricating composition, of an organoammonium salt of a Group VI metal, comprising the reaction product of a metal acid hydrate of formula $MO_4H_2 \cdot H_2O$ with at least one alkyl amine of the formula $R^1R^2$ NH wherein $R^1$ and $R^2$ may be identical or different and comprise at least one linear or branched, saturated or unsaturated $C_8$-$C_{40}$ alkyl group, wherein M is tungsten.

2. The lubricating composition of claim 1, wherein the concentration of the organoammonium salt is between about 0.05 to 2.0 wt.-%.

3. The lubricating composition of claim 2, wherein the concentration of the organoammonium salt is between about 0.09 to 0.5 wt.-%.

4. The lubricating composition of claim 1 wherein $R^1$ and $R^2$ may be identical or different and $R^1$ or $R^2$ comprises at least one linear or branched, saturated or unsaturated $C_{8-13}$ alkyl group.

5. The lubricating composition of claim 1 wherein $R^1$ and $R^2$ comprise at least one $C_8$ alkyl group.

6. The lubricating composition of claim 1 wherein $R^1$ and $R^2$ comprise at least one $C_{13}$ alkyl group.

7. The lubricating composition of claim 1 wherein the $R^1R^2$NH comprises di-tridecylamine.

8. The lubricating composition of claim 7 wherein the organoammonium salt comprises di-tridecylammonium tungstate.

9. The lubricating composition of claim 1 wherein the $R^1R^2$ NH comprises di-n-octylamine.

10. The lubricating composition of claim 9 wherein the organoammonium salt comprises di-n-octylammonium tungstate.

* * * * *